United States Patent [19]
Min et al.

[11] Patent Number: 5,985,609
[45] Date of Patent: Nov. 16, 1999

[54] PROCESS FOR PREPARING HEPATITIS C VIRUS ENVELOPE GLYCOPROTEINS

[75] Inventors: Mi-Kyung Min; Joon-Sang Park, both of Seoul; Jung-Seob Kim, Suwon; Yung-Dae Yun, Seoul; Hong-Mo Moon, Seohyun-Dong, all of Rep. of Korea

[73] Assignee: Mogam Biotechnology Research Institute, Kyonggi-Do, Rep. of Korea

[21] Appl. No.: 08/334,545

[22] Filed: Nov. 4, 1994

[51] Int. Cl.$^6$ .............................. C12N 15/51; C12Q 1/70; C07H 21/04
[52] U.S. Cl. .............................. 435/69.3; 435/5; 435/358; 536/23.72
[58] Field of Search .............................. 435/5, 69.3, 358; 536/23.72

[56] References Cited

FOREIGN PATENT DOCUMENTS 0521318  1/1993  European Pat. Off. ........ C12N 15/51

OTHER PUBLICATIONS

M.M. Hulst et al.—Glycoprotein E1 of Hog Cholera Virus Expressed in Insect Cells Protects Swine from Hog Choler, J. Virol., 67 (9): 5435–5442 (1993).

P. Despres et al.—Recombinant Baculoviruses Expressing Yellow Fever Virus E and NS1 proteins Elicit Protective Immunity in Mice, J. Gen. Virol., 72:2811–2816 (1991).

A. Grakoui et al.—Expression and Identification of Hepatitis C Virus Polyprotein Cleavage Products, J. Virol., 67(3):1385–1395 (1993).

N. Kato et al.—Molecular Cloning of the Human Hepatitis C Virus Genome from Japanese Patients with Non–A, Non–B Hepatitis, proc.Natl.Acad.Sci., USA, 87:9524–9528 (1990).

J. Schlesinger et al.—Protection against Yellow Fever in Monkeys by Immunization with Yellow Fever Virus Nonstructural Proteins NS1, J. Virol., 60(3):1153–1155 (1986).

M. Hijikata et al.—Gene Mapping of the Putative Structural Region of the Hepatitis C Virus Genome by in vitro Processing Analysis, proc.Natl.,Acad.Sci., USA, 88:5547–5551 (1991).

Q–L. Choo et al.—Genetic Organization and Diversity of the Hepatitis C Virus, Proc.Natl.Acad.Sci., USA, 88:2451–2455 (1991).

H.J. Alter—Transfusion–Associated Non–A, Non–B Hepatitis: The First Decade, Viral Hepatitis and Liver Disease, 537–542 (1988).

Q.L. Choo et al.—Hepatitis C Virus: The Major Causitive Agent of Viral Non–A, Non–B Hepatitis, British Medical Bulletin, 46(2):423–441 (1990).

Q–L. Choo et al.—Isolation of a cDNA Clone Derived from a Blood–Borne Non–A, Non–B, Hepatitis Genome, Science, 244:359–362 (1989).

E. Weiland et al.—Pestivirus Glycoprotein Which Induces Neutralizing Antibodies Forms Part of a Disulfide–Linked Heterodimer, J. Virol., 64(8):3563–3569 (1990).

B. Falgout et al.—Immunization of Mice with Recombinant Vaccinia Virus Expressing Authentic Dengue Virus Non-structural Protein NS1 Protects against Lethal Dengue Virus Encephalitits, J. Virol., 64(9):4356–4363 (1990).

T. Rumenapf et al.—Structural Proteins of the Hog Cholera Virus Expressed by Vaccinia Virus: Further Characterization and Induction of Protective Immunity, J. Virol., 65(2):589–597 (1991).

R.H. Miller and R.H. Purcell—Hepatitis C Virus Shares Amino Acid Sequence Similarity with Pestiviruses and Flaviviruses As Well As Members of Two Plant Virus Supergroups, Proc.Natl.,Acad.Sci., USA, 37:2057–2061 (1990).

M. Hijikata et al.—Proteolytic Processing and Membrane Association of Futative Nonstructural Proteins of Hepatitis C Virus, Proc.Natl.Acad.Sci., USA, 90:10773–10777.

J.S. Park et al.—Abstracts, 2nd International Meeting on Hepatitis C and Related Viruses, Jul. 31–Aug. 5, 1994.

Invitrogen Catalog, pp. 49–50 (1994).

Spalete et al., "Characterization of the Hepatitis C Virus E2/NS1 Gene Product Expressed in Mammalian Cells", Virology 188:819–30 (1992).

*Primary Examiner*—Michael P. Woodward
*Attorney, Agent, or Firm*—Darby & Darby

[57] ABSTRACT

The present invention relates to a novel process for preparing hepatitis C virus (HCV) envelope glycoproteins employing Chinese Hamster Ovary (CHO) cells transformed with recombinant expression vectors containing the hepatitis C virus genome. The present invention provides CHO cells cotransfected with DHFR (dihydrofolate reductase) minigene pDCHIP and recombinant expression vectors containing cDNAs of HCV E1 and E2/NS1 ligated with tissue plasminogen activator signal sequence. HCV E1 and E2/NS1 envelope glycoproteins are produced in a massive manner from the transformed CHO cells adapted in methotrexate. The HCV envelope glycoproteins produced by the present invention can be applied to the development of a diagnostic reagent and a potential preventive HCV vaccine.

6 Claims, 11 Drawing Sheets

FIG. 1(A)

```
TACGAGGTGC GCAACGTGTC CGGGATATAC CATGTCACGA ACGACTGCTC CAACGCAAGC

ATTGTGTATG AGGCAGCGGA CTTGATTATG CATACCCCCG GGTGCCGTGCC CTGCCGTTCGG

GAGAGCAATA TTTCCCGTTG CTGGGTAGCG CTCACTCCCA CGCTCGCCGGC CAGGAACGCC

ACCGTCCCCA CCACGACAAT ACGACGCCAC GTCGATTTGC TCGTTGGGGC GGCAGCTTTC

TGCTCCGCTA TGTACGGTGGG AGACCTTTGC GGATCCGTTT TCCTCGTCTC CCAGTTGTTC

ACCTTTTCGC CTCGTCAGCA TGAGACGTTA CAGGACTGCA ACTGCTCAAT CTATCCCCGC

CACTTGTCAG GTCACCGCAT GGCATGGGAC ATGATGATGA ACTGGTCACC TACAACAGCC

CTACTACTGT CGCACTTACT CCGGATCCCA CAAGCTGTCT TGGACATGGT GGCAGGGGCC

CACTGGGGAG TCCTGGCGGG CCTCGCCTAC TATTCCATGG TGGGGAACTG GGCTAAGGTT

TTGATTGTGG TGCTGCTCTT TGCTGGCGTT GACGGG
```

FIG. 1(B)

```
CACACCCACG TGACAGGGGG AACGGCAGCC TATAACACCC GTGGGCTCAC AAGCCTCTTT
ACATTTGGGC CGTCTCAGAA AATCCAACTC ATAAATATTA ATGGCAGTTG GCACATCAAC
AGGACTGCCC TAAAACTGCAA TGACTCCCTC CAAACTGGGT TTATTGCCGC GCTGTTCTAT
ACGCGCAGTT TCAACGCGTC CGGATGCCCA GAGGCAGTGG CCAGTTGCCG CCCCATTGAC
AAGTTCGACC AGGGGTGGGG TTCCATCACC TATGCCCGAGC CTGACAGCCT GGACCAGAGG
CCTTATTGCT GGCACTACCC ACCCCGACAG TGTGGTATCG TGCCAGCCGTC GCAGGTGTGT
GGTCCGGTGT ATTGCTTCAC CCCGAGCCCT GTTGTCGTGG GGACGACCGA TCGGTTCGGT
GTCCCTACGT ATAGCTGGGG GGAGAACGTG ACTGATGTGC TGCTCCTTAA CAACACGCGG
CCGCCCCACA AGGACTGGTT CGGCTGTACA TGGATGAATA GCACTGGGTT CACCAAGACG
```

FIG. 1(C)

```
TGCGGGGGGC CCCGCTGTAA CATCGGGGGG GCCGGCAACT ACACCTTGAC CTGCCCCACG
GACTGCTTCC GGAAGCACCC TGGGGCCACT TACACAAAAT GTGGTTCGGG GCCTTGGTTG
ACGCCTAGGT GCTTAGTTGA TTACCCATAC AGGCTATGGC ACTACCCCTG CACTGTCAAT
TTTTCCATCT TCAAGGTCAG GATGTACGTG GGGGGCGTGG AGCACAGGCT CAACGCTGCA
TGCAATTGGA CGCGAGGAGA GCGTTGTGCT TTGGAGGACA GGGATAGGTC GGAGCTCAGC
CCGCTGCTAC TGTCTACAAC AGAGTGGCAG ACGCTGCCCT GCTCCTTCAC CACCCTACCC
GCTTTGTCCA CTGGCTTGAT CCATCTCCAT CAGAACATTG TGGACATCCA ATACCTGTAC
GGTATAGGGT CAGCCAGTTGT CTCCCTTTGCA ATCAGATGGG AGTATGTCCT GTTGCTTTTC
CTTCTCCTGG CGGACGCCGCG CGTCTGCGCC TGCTTGTGGA TGATGCTGCT GATAGCCCAG
GCTGAGGCCA CCTTAGAGAA
```

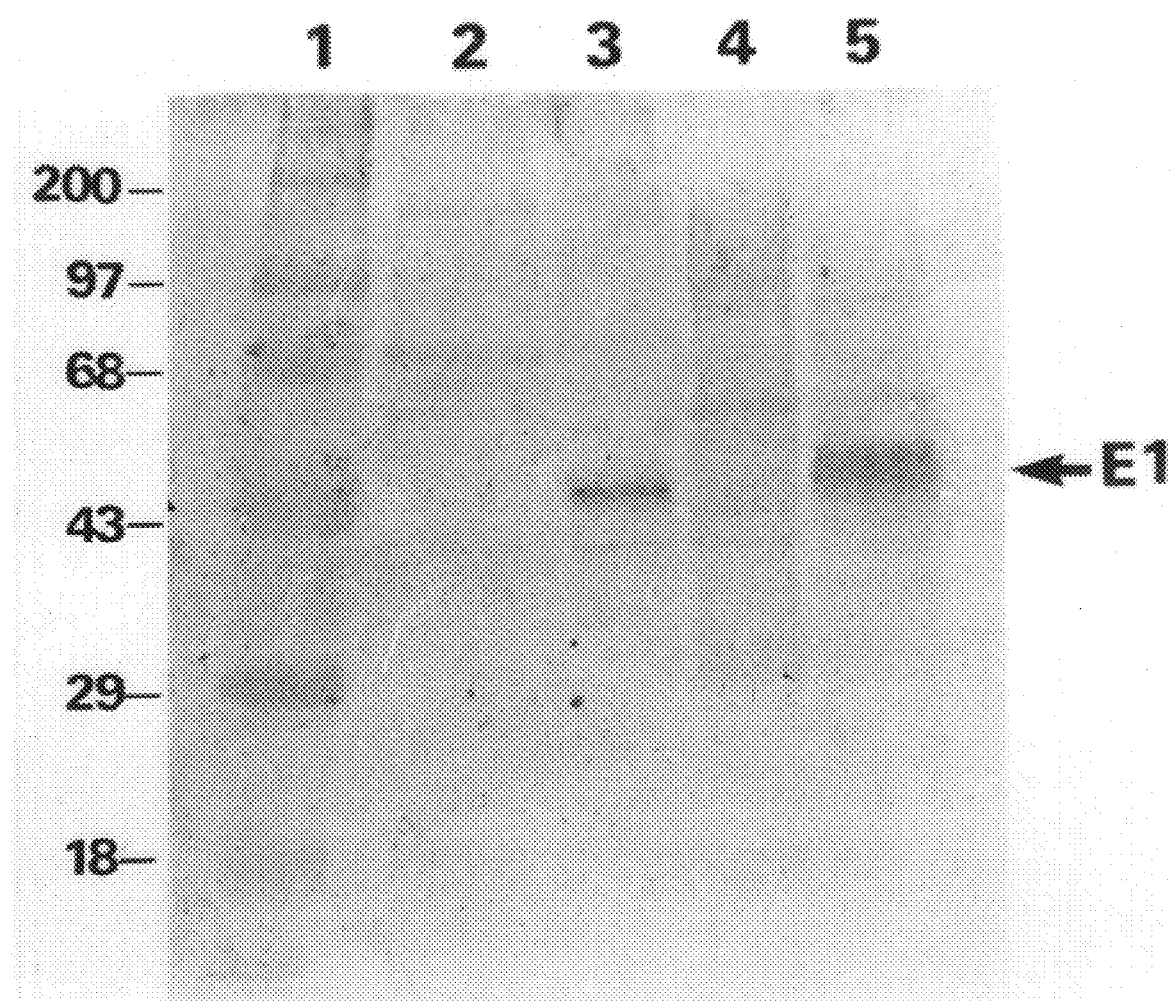

PROCESS FOR PREPARING HEPATITIS C VIRUS ENVELOPE GLYCOPROTEINS

FIELD OF THE INVENTION

The present invention relates to a novel process for preparing hepatitis C virus envelope glycoproteins employing Chinese Hamster Ovary cells transformed with recombinant expression vector containing the hepatitis C virus genome.

BACKGROUND OF THE INVENTION

Hepatitis C virus (hereinafter referred to as 'HCV') is a major etiologic agent for the post transfusional and sporadic non-A, non-B hepatitis which develops into hepatocellular carcinoma through chronic hepatitis and liver cirrhosis in more than 50% of the cases (see: Alter, H. J., Transfusion-associated non-A, non-B hepatitis: the first decade, In A-J Zuckerman Ed. (1988); Choo Q. L. et al., Science, 244:359–362 (1989); Choo Q. L. et al., British Medical Bulletin, 46 (2):423–441 (1990)). Considering its seriousness due to high mortality and morbidity, much interests have been centered on the development of a diagnostic reagent and a vaccine for HCV infection. Although much progress has been made at the molecular level since a whole HCV genome was cloned and nucleotide sequences were analysed (see: Choo Q. L. et al., Proc. Natl. Acad. Sci., USA, 88:2451–2455 (1991); Kato, N. et al., Proc. Natl. Acad. Sci., USA, 87:9524–9528 (1990)), the difficulty of obtaining enough free viruses either from in vitro propagation or blood of HCV infected patient has been a barrier in development of conventional vaccine including whole killed or attenuated viral vaccine. Under the circumstances, heterologous expression system has been considered to be the best choice to obtain useful HCV antigens as components of HCV subunit vaccine.

On the other hand, HCV has a 9.4 kb single-stranded positive sense RNA genome which encodes a single polyprotein of about 3,010 amino acids (see: Choo Q. L. et al., Proc. Natl. Acad. Sci., USA, 88:2451–2455 (1991); Takamizawa, A. et al., J. Virol., 65:1105–1113 (1991); Kato, N. et al., Proc. Natl. Acad. Sci., USA, 87:9524–9528 (1990)). This single large polypeptide is co- or post-translationally processed to at least 9 polypeptides including two putative envelope proteins (E1 and E2/NS1) either by host signalase or viral proteases (see: Hijikata, M. et al., Proc. Natl. Acad. Sci., USA, 88:5547–5551 (1991); Hijikata, M. et al., Proc. Natl. Acad. Sci., USA, 90:10773–10777 (1993); Grakoui, A. et al., J. Virol., 67 (3): 1385–1395 (1993)). Hydropathy analysis of the deduced amino acid sequences of the HCV poly-protein showed the relatedness of HCV with pestiviruses and flaviviruses (see: Miller, R. H. and Purcell, R. H., Proc. Natl. Acad. Sci., USA, 87:2057–2061 (1990)).

In this regard, there have been several reports indicating that antibodies for the envelope glycoproteins of pestiviruses and flaviviruses (E1 and E2, E1 and NS1, respectively) protect their host against infection (see: Rumenapf, T. et al., J. Virol., 65 (2):589–597 (1991); Falgout, B. et al., J. Virol., 64 (9):4356–4363 (1990); Weiland, E. et al., J. Virol., 64 (8):3563–3569 (1990); Schlesinger, J. J. et al., J. Virol., 60 (3):1153–1155 (1986); Hulst, M. M. et al., J. Virol., 67 (9):5435–5442 (1993); Despres, P. et al., J. Gen. Virol., 72:2811–2816 (1991)). In the case of flavivirus, effective attenuated vaccines have been developed and more recently, recombinant based vaccines directed against flaviviruses and pestiviruses are under investigation (see: Rumenapf, T.

et al., J. Virol., 65:589–597 (1991)). Further, two putative envelope glycoproteins (E1 and E2/NS1) of HCV, identified by in vitro processing analyses and N-terminal amino acid sequence analysis, have been expected to be the most probable components of preventive subunit vaccine considering that these may play a major role in the course of viral infection and host immune responses.

Accordingly, there is a need in the art for the development of a practical process for mass production of HCV E1 and E2/NS1 envelope glycoproteins for a diagnostic reagent and a potential preventive HCV vaccine.

SUMMARY OF THE INVENTION

In accordance with the present invention, the inventors developed a novel process for preparing HCV E1 and E2/NS1 envelope glycoproteins by employing Chinese Hamster Ovary (hereinafter referred to as 'CHO') cells transformed with recombinant vectors for said E1 and E2/NS1 gene expression.

A primary object of the present invention is, therefore, to provide novel CHO cell lines transformed with the recombinant vectors for HCV E1 and E2/NS1 expression.

Another object of the present invention is to provide a novel process for preparing HCV E1 and E2/NS1 envelope glycoproteins from CHO cells transformed with the said recombinant expression vectors.

BRIEF DESCRIPTION OF DRAWINGS

The above and the other objects and features of the present invention will become apparent from following descriptions given in conjunction with the accompanying drawings, in which:

FIG. 1(A) is the nucleotide sequence of HCV E1 gene (SEQ ID NO:1);

FIGS. 1(*b*) and (*c*) is the nucleotide sequence of HCV E2/NS1 gene (SEQ ID NO:2);

FIG. 2(A) is a construction scheme for tPA (tissue plasminogen activator)-E1 cDNA gene fragment from HCV genome;

FIG. 2(B) is a construction scheme for tPA (tissue plasminogen activator)-E2/NS1 cDNA gene fragment from HCV genome;

FIG. 3(A) is a photograph showing immunoblot analysis results of intra- and extracellular forms of HCV E1 expressed by HCV E113 cell lines adapted at different concentrations of methotrexate;

FIG. 3(B) is a photograph showing immunoblot analysis results of increased amount of extracellular HCV E1 expressed by HCV E113 cell lines adapted at different concentrations of methotrexate;

FIG. 4(A) is a photograph showing immunoblot analysis results of intra- and extracellular forms of HCV E2/NS1 expressed by HCV E219 cell lines adapted at different concentrations of methotrexate;

FIG. 4(B) is a photograph showing immunoblot analysis results of increased amount of extracellular HCV E2/NS1 expressed by HCV E219 cell lines adapted at different concentrations of methotrexate;

FIG. 5(A) is a immunofluorescence photograph of DHFR (dihydrofolate reductase) -positive CHO cells;

FIG. 5(B) is a immunofluorescence photograph of stable recombinant HCV E113 cell lines;

FIG. 5(C) is a immunofluorescence photograph of stable recombinant HCV E219 cell lines;

FIG. 6(A) is a photograph showing immunoblot analysis results of HCV E1 expressed from HCV E113 cell lines treated with tunicamycin; and, FIG. 6(B) is a photograph showing immunoblot analysis results of HCV E2/NS1 expressed from HCV E219 cell lines treated with tunicamycin.

DETAILED DESCRIPTION OF THE INVENTION

Figure 2A:
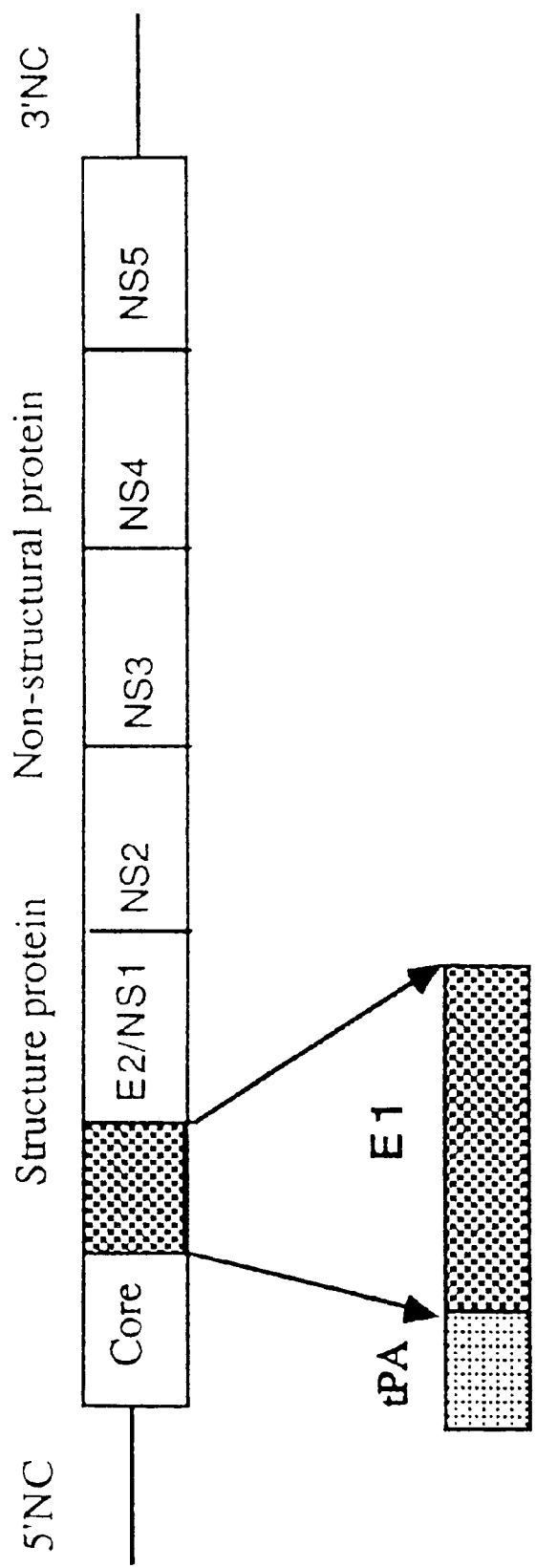
Figure 2:
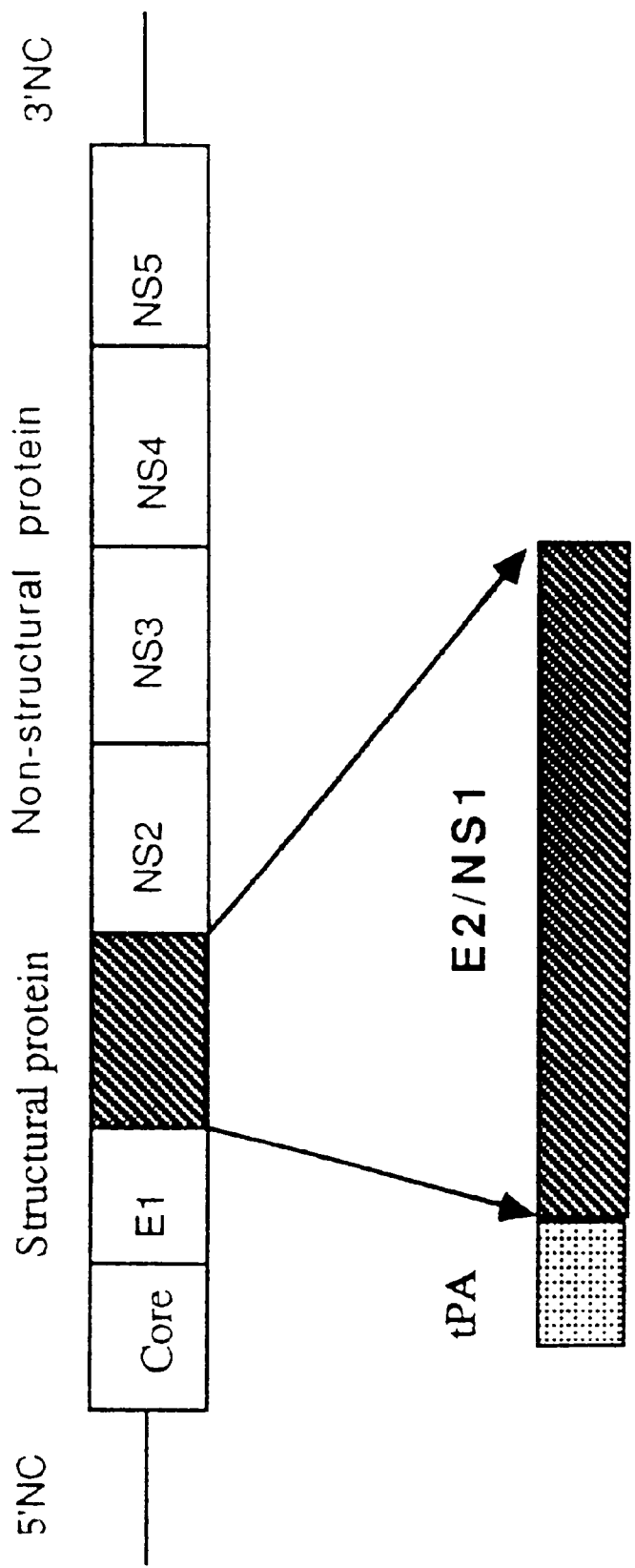

To prepare HCV E1 and E2/NS1 cDNAs, RNA was extracted from plasmas of anti-HCV seropositive but anti-HBsAg seronegative patients and cDNA synthesis was followed. cDNA was amplified by polymerase chain reaction (hereinafter referred to as 'PCR') using external primer pairs and internal primer pairs. cDNAs of HCV E1 (903–1479 nucleotide) and E2/NS1 (1480–2579 nucleotide) thus prepared were ligated either with or without tissue plasminogen activator (hereinafter referred to as 'tPA') signal sequence at their 5'ends and inserted into the EcoRV site of the pcDNA1/Amp vector to prepare recombinant expression vectors. The nucleotide number of HCV gene was given according to Kato's numbering system (see: Kato, N. et al., Proc. Natl. Acad. Sci., USA, 87:9524–9528 (1990)).

The present inventors discovered the HCV E1 and E2/NS1 genes employed in the invention is novel; and, employed dihydrofolate reductase (hereinafter referred to as 'DHFR') deficient CHO cells/CMV (cytomegallovirus promoter) system for the expression of HCV E1 and E2/NS1 envelope glycoproteins. The recombinant expression vectors were cotransfected with DHFR minigene pDCHIP into DHFR deficient CHO cells (DG44) by the Lipofectin mediated transfection technique.

To construct stable transformed CHO cells, the transformed DHFR-positive CHO cells were first screened in selection medium of nucleoside free-MEM supplemented with 10% fetal calf serum. The foci, formed after 10–14 days growth in selection media, were picked by cylinder cloning and propagated either individually or in a pool. The picked stable transformed CHO cells were subjected to the stepwise selection in progressively increasing concentrations of methotrexate (hereinafter referred to as 'MTX'). Several rounds of selection with the MTX gave stable HCV E1 and E2/NS1 transformed cell lines. It was determined from Southern blot analysis that the the HCV E1 and E2/NS1 genes were inserted at several random sites of CHO cell genome and progressively amplified according to concentration of the MTX.

Immunoblot analysis revealed that the expression level from the stable transformed cell lines was much higher for the expression vectors containing the tPA signal sequence than those without the tPA signal sequence. The recombinant CHO cell lines containing the tPA signal sequence were used for further analyses in the present invention. The HCV E1 and E2/NS1 genes were expressed with fusion of the tPA signal sequence to promote the processing and secretion of E1 and E2/NS1 proteins. Expressed E1 and E2/NS1 proteins were found intra- and extracellular when they had the tPA signal sequence; and, it was also determined that the diverse sizes of HCV E1 and E2/NS1 expressed by transformed CHO cells were attributed to N-linked glycosylation by the treatment with tunicamycin of the recombinant CHO cell lines.

In accordance with the present invention, HCV E1 and E2/NS1 envelope glycoproteins can be produced in a massive manner from the transformed CHO cells; and, therefore, the recombinant HCV E1 and E2/NS1 envelope glycoproteins of the invention can be applied to the developement of a diagnostic reagent and a potential preventive HCV vaccine.

The present invention is further illustrated in the following examples, which should not be taken to limit the scope of the invention.

EXAMPLE 1

Preparation of HCV E1 and E2/NS1 cDNAs

To isolate and amplify HCV E1 and E2/NS1 genes, RNA was extracted by GITC (guanidinium isothiocyanate)-phenol method from 0.2 ml each of plasmas from anti-HCV seropositive but anti-HBsAg seronegative patients (see: Chirgwin, J. M. et al., Biochemistry, 18:5294–5304 (1979)). cDNA was synthesized using the reverse transcriptase; and, amplified by 30 cycles of PCR (94° C. for 90 sec, 45° C. for 90 sec, 72° C. for 2 min) using the following external primer pairs. Amplification product (10 μl) was reamplified under the same conditions using the following internal primer pairs.

The external primer sets for E1 gene fragment were:

5'-CAGGGAATCTGCCCGGTTGC-3' for the positive strand (SEQ ID NO:3); and,

5'-GATGTGCCAGCTGCCGTTGG-3' for the negative strand (SEQ ID NO:4).

The internal primer sets for E1 gene fragment were:

5'-TACGAGGTGCGCAACGTGTC-3' for the sense strand (SEQ ID NO:5); and,

5'-CCCGTCAACGCCAGCAAAGA-3' for the antisense strand (SEQ ID NO:6).

The external primer sets for E2/NS1 gene fragment were:

5'-TCTTTGCTGGCGTTGACGGG-3' for the positive strand (SEQ ID NO:7); and,

5'-GCCGCATTGAGGACCACCAG-3' for the negative strand (SEQ ID NO:8).

The internal primer sets for E2/NS1 gene fragment were:

5'-CACACCCACGTGACAGGGGG-3' for the sense strand (SEQ ID NO:9); and,

5'-GTTCTCTAAGGTGGCCTCAG-3' for the antisense strand (SEQ ID NO:10).

In HCV E1 gene amplification, a single band of 767 bp after the first round of PCR and of 576 bp after the second round of PCR was visible in 1% agarose gel by ethidium bromide staining. The 576 bp DNA framents were electroeluted from a 2% LMT agarose gel and treated with Klenow enzyme to make blunt end and then cloned into a SmaI site of pUC19 (New England Biolabs, Inc., USA) or pUC119 (see: Vieira, J. and Messing, J., Methods Enzymol., 153:6–11 (1987)) for sequence analysis. The recombinant plasmid was named with pUCE1, which has the HCV E1 gene encoding from Tyr192 to Gly383. Dideoxy sequencing was performed on single standed and/or double stranded template using a Sequenase DNA Sequencing Kit (USB Corp., USA); and, the nucleotide sequence of HCV E1 gene, which has 74% homology with HCV1 (US) and 92% homology with HCVJ (Japan), was showed in FIG. 1(A).

In HCV E2/NS1 gene amplification, a single band of 1140 bp after the first round of PCR and of 1100 bp after the second round of PCR was visible. The 1100 bp DNA fragments were electroeluted and cloned into a SmaI site of pUC19 or pUC119 for sequence analysis. The recombinant plasmid was named with pUCE2/NS1, which has the HCV E2/NS1 gene encoding from His384 to Asn750. The nucleotide sequence of HCV E2/NS1 gene, which has 72% homology with HCV1 (US) and 87% homology with HCVJ (Japan), was showed in FIG. 1(B).

EXAMPLE 2

Construction of Expression Vectors

The HCV E1 and E2/NS1 genes employed for expression were prepared from the pUCE1 and pUCE2/NS1 by the PCR using the following oligonucleotide primers which were designed to have an ATG initiation codon and a TGA termination codon.

The primer sets for the E1 gene fragment were:

5'-GAGCTCGGATCCATGTACGAGGTGCGCAACGTGTC-3' for the positive strand (SEQ ID NO:11); and,

5'-GAGCTCGGATCCTCACCCGTCAACGCCAGCAAAGA-3' for the negative strand (SEQ ID NO:12).

The primer sets for the E2/NS1 gene fragment were:

5'-GAGCTCGGATCCATGCACACCCACGTGACAGGGGG-3' for the positive strand (SEQ ID NO:13); and,

5'-GAGCTCGGATCCTCAGTTCTCTAAGGTGGCCTCAG-3' for the negative strand (SEQ ID NO:14).

For the modification with the tPA signal sequence, HCV E1 and E2/NS1 genes were prepared from the pUCE1 and pUCE2/NS1 by the PCR using the following oligonucleotide primers. The oligonucleotide primers lacking the ATG initiation codon were used, because the tPA signal sequence has its own ATG codon.

The positive strand oligonucleotide primers were:

5'-TACGAGGTGCGCAACGTGTC-3' for the E1 gene fragment (SEQ ID NO:15); and,

5'-CACACCCACGTGACAGGGGG-3' for the E2/NS1 gene fragment (SEQ ID NO:16).

The tPA signal sequence was derived from pBMT3X containing the full genome of tPA by the PCR and ligated to the 5' end of HCV E1 and E2/NS1 gene fragment to obtain tPA-E1 and tPA-E2/NS1 cDNAs conserving the open reading frame (see: FIGS. 2(A) and 2(B)).

The primer sets for the tPA signal sequence were:

5'-GACTGAATTCATGGATGCAATGA-3' for the positive strand (SEQ ID NO:17); and,

5'-ACTGAAATCTCTGGCTCCTCTT-3' for the negative strand (SEQ ID NO:18).

The cDNA gene fragments thus obtained, i.e., E1, E2/NS1, tPA-E1 and tPA-E2/NS1, were eluted from a 2% LMT agarose gel and were inserted into the EcoRV site of the pcDNA1/Amp vector (Invitrogen, USA), which were named with pcDNA1/AmpE1, pcDNA1/AmpE2/NS1, pcE1/Amp and pcE2/Amp, respectively. The nucleotide sequence analysis was undertaken for the junction of each gene fragment to verify the right open reading frame. The recombinant expression vectors designated as pcDNA1/AmpE1, pcDNA1/AmpE2/NS1, pcE1/Amp and pcE2/Amp were cotransfected with DHFR minigene pDCHIP (see: Carlos J. Ciudad et al., J. Biol. Chem., 263:16274–16282 (1988)) into DHFR deficient CHO cells (DG44) (see: Urlaub, G. et al., Somatic Cell Mol. Gen., 12:555–666 (1986)) by the Lipofectin mediated transfection technique.

EXAMPLE 3

Construction of Recombinant CHO Cells

After transfection of DHFR deficient CHO cells (DG44) with each recombinant expression vector and DHFR minigene pDCHIP, the transformed DHFR-positive CHO cells were first screened in selection medium of nucleoside free-αMEM supplemented with 10% fetal calf serum dialysed in phosphate-buffered saline. 20–100 colonies per 35 mm dish were formed after 10–14 days growth in selection media. The recombination rate was determined to be 1–3% depending on the ratio of HCV E1 or E2/NS1 expression vector and DHFR minigene. Twenty colonies were individually subjected to the stepwise selection in progressively increasing concentrations of MTX (from 10 nM to 10 $\mu$M). The remaining colonies were pooled and treated as for individual colony. Several rounds of selection with the MTX gave 2 individual and 1 pool of HCV E1 and E2/NS1 transformed cells lines. The stable transformed cell lines were designated as HCV E17, HCV E113, HCV E1P11 for the HCV tPA-E1 clones and HCV E211, HCV E219, HCV E2P22 for the HCV tPA-E2/NS1 clones.

Similar recombination results were obtained for recombinant expression vectors lacking a tPA signal sequence. The expression level of HCV E1 and E2/NS1 was much higher for the expression vectors containing the tPA signal sequence than those without the tPA signal sequence. Recombinant CHO cell lines containing the tPA signal sequence (i.e., HCV E17, HCV E113, HCV E1P11; and, HCV E211, HCV E219, HCV E2P22) were used for further analyses in the present invention.

To verify the amplification of HCV E1 and E2/NS1 genes after several rounds of selection with increasing concentrations of the MTX (form 10 nM to 10 nM), Southern blot analysis of genomic DNA was performed. Genomic DNA was prepared from each transformed CHO cell in accordance with the modified method of Blin and Stafford (see: Blin, N. and D. W. Stafford, Nucleic Acids Res., 3:2303 (1976)) and digested with BamH1. The fractionated DNA fragments in a 0.8% agarose gel were transferred to nitrocellulose membrane. Hybridization was undertaken with the nick-translated E1 or the E2/NS1 or the DHFR gene probe using a conventional procedure in the art. Southern blot analysis showed that: the HCV E1 and E2/NS1 genes were inserted at several random sites of CHO cell genome; and progressively amplified as the concentrations of MTX were increased. The restriction pattern of the genomic DNA derived from each transformed CHO cell line did not change after selection of certain concentration of MTX, which indicated that they became molecularly stable.

EXAMPLE 4

Expression of HCV E1 and E2/NS1 Proteins

The HCV E1 and E2/NS1 recombinant CHO cell lines (i.e., HCV E17, HCV E113, HCV E1P11; and, HCV E211, HCV E219, HCV E2P22), adapted in MTX, were grown in a T-25 flask to prepare cell lysates and the culture supernatant. The culture supernatant was ultracentrifuged at 25,000 rpm for 1 hr to generate a pellet of secreted protein. Cell lysates and the pellet of secreted proteins were subjected to electrophoresis on 10% SDS-PAGE. One gel was stained with Coomassie blue R and the other was subjected to blotting to a nitocellulose membrane for immunoblot analysis. Immunoblot analysis was undertaken using the anti-HCV seropositive but anti-HBV seronegative patient sera as a primary antibody in 1:100 dilution and horse radish peroxidase conjugated goat anti-human IgG (Kirkegard and Perry Laboratory, USA) as the secondary antibody in 1:2500 dilution.

Each HCV E1 recombinant cell line showed similar or comparable amount of HCV E1 expression as determined by immunoblot analysis and the same result was obtained in case of HCV E2/NS1 recombinant CHO cell lines. However, it was determined that HCV E113 and HCV E219 cell lines showed the most stable growth pattern; and, therefore, the said cell lines were selected for further experiments. The said cell lines were named with E113 and E219, respectively; and deposited with the Korean Cell Line Research Foundation (KCLRF), an International Depositary Authority (IDA), on Sep. 5, 1994 as deposition Nos. KCLRF-BP-00003 and KCLRF-BP-00004.

To determine HCV E1 and E2/NS1 expression from recombinant CHO cell lines depending upon concentration of MTX, immunoblot analysis was undertaken by employing the HCV E113 and HCV E219 cell lines adapted at increased concentrations of the MTX to the level of 4 $\mu$M–5 $\mu$M.

Figure 3A:
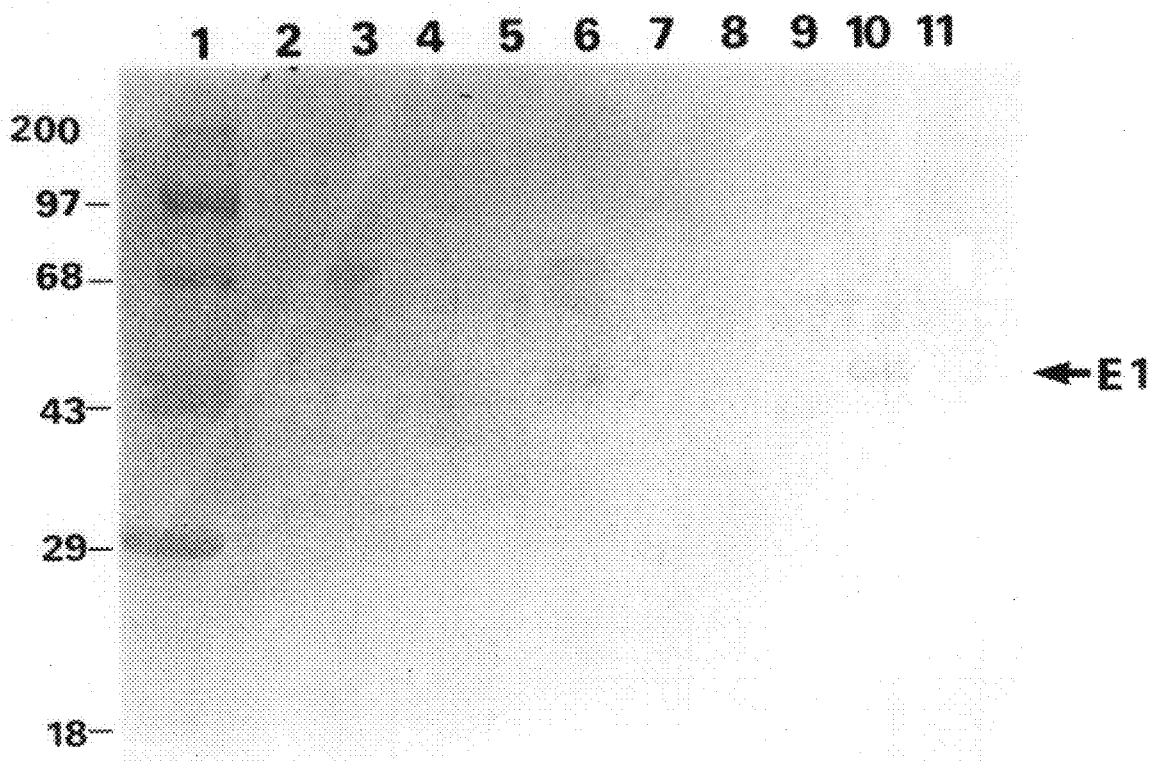

FIG. 3(A) shows immunoblot analysis results for HCV E1 envelope glycoprotein expressed from HCV E1 stable cell line, i.e., HCV E113. In FIG. 3(A), lane 1 is high molecular protein markers; lane 2 is the cuture supernatant of nontransformed DHFR deficient CHO cells; lane 3 is the culture supernatant of DHFR-positive CHO cells; lane 4 is the culture supernatant of HCV E113 adapted at 500 nM MTX; lane 5 is the culture supernatant of HCV E113 adapted at 1 $\mu$M MTX; lane 6 is the culture supernatant of HCV E113 adapted at 5 $\mu$M MTX; lane 7 is cell lysate of nontransformed DHFR deficient CHO cells; lane 8 is cell lysate of DHFR-positive CHO cells; lane 9 is cell lysate of HCV E113 adapted at 500 nM MTX; lane 10 is cell lysate of HCV E113 adapted at 1 $\mu$M MTX; and, lane 11 is cell lysate of HCV E113 adapted at 5 $\mu$M MTX. As can be seen in FIG. 3(A), the molecular size of HCV E1 proteins ranges from 33 kDa to 45 kDa in both the culture supernatant and cell lysate (33 kDa–45 kDa protein bands for HCV E1 are around indicated arrow head).

To clarify secretion of HCV E1 expressed from HCV E113, immunoblot analysis was carried out again by employing increased amount of extracellular protein (see: FIG. 3(B)). In FIG. 3(B), lanes are the same as lane 1, 2, 3, 4 and 5 in FIG. 3(A) except for the amount of loaded sample. As can be seen in FIG. 3(B), the molecular size of HCV E1 proteins ranges from 33 kDa to 45 kDa in the culture supernatant (33 kDa–45 kDa protein bands for HCV E1 are around indicated arrow head).

Figure 4A:
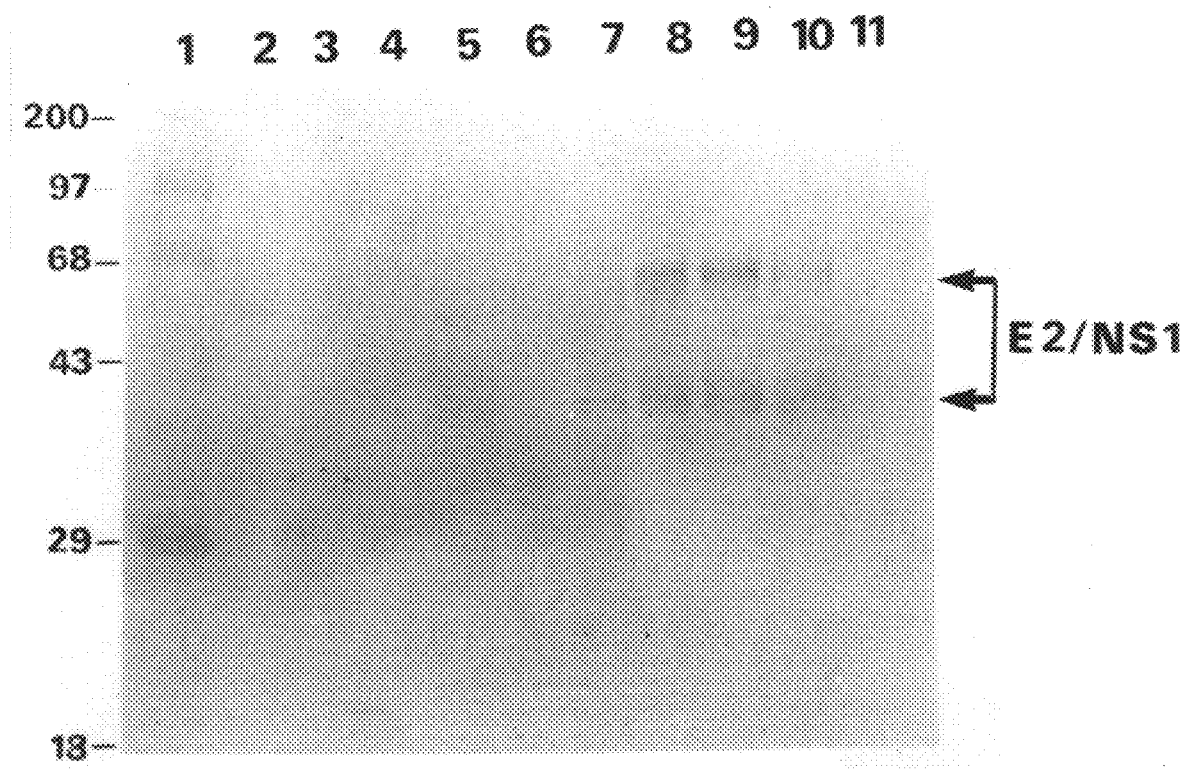

FIG. 4(A) shows immunoblot analysis results for HCV E2/NS1 envelope glycoprotein expressed from HCV E2/NS1 stable cell line, i.e., HCV E219. In FIG. 4(A), lane 1 is high molecular protein markers; lane 2 is the culture supernatant of nontransformed DHFR deficient CHO cells; lane 3 is the culture supernatant of DHFR-positive CHO cells; lane 4 is the culture supernatant of HCV E219 adapted at 500 nM MTX; lane 5 is the culture supernatant of HCV E219 adapted at 1 $\mu$M MTX; lane 6 is the culture supernatant of HCV E219 adapted at 4 $\mu$M MTX; lane 7 is cell lysate of nontransformed DHFR deficient CHO cells; lane 8 is cell lysate of DHFR-positive CHO cells; lane 9 is cell lysate of HCV E219 adapted at 500 nM MTX; lane 10 is cell lysate of HCV E219 adapted at 1 $\mu$M MTX; and, lane 11 is cell lysate of HCV E219 adapted at 4 $\mu$M MTX. As can be seen in FIG. 4(A), the molecular size of HCV E2/NS1 proteins ranges from 42 kDa to 72 kDa in both the culture supernatant and cell lysate (42 kDa–72 kDa protein bands for HCV E2/NS1 are indicated by arrow heads).

Figure 4B:
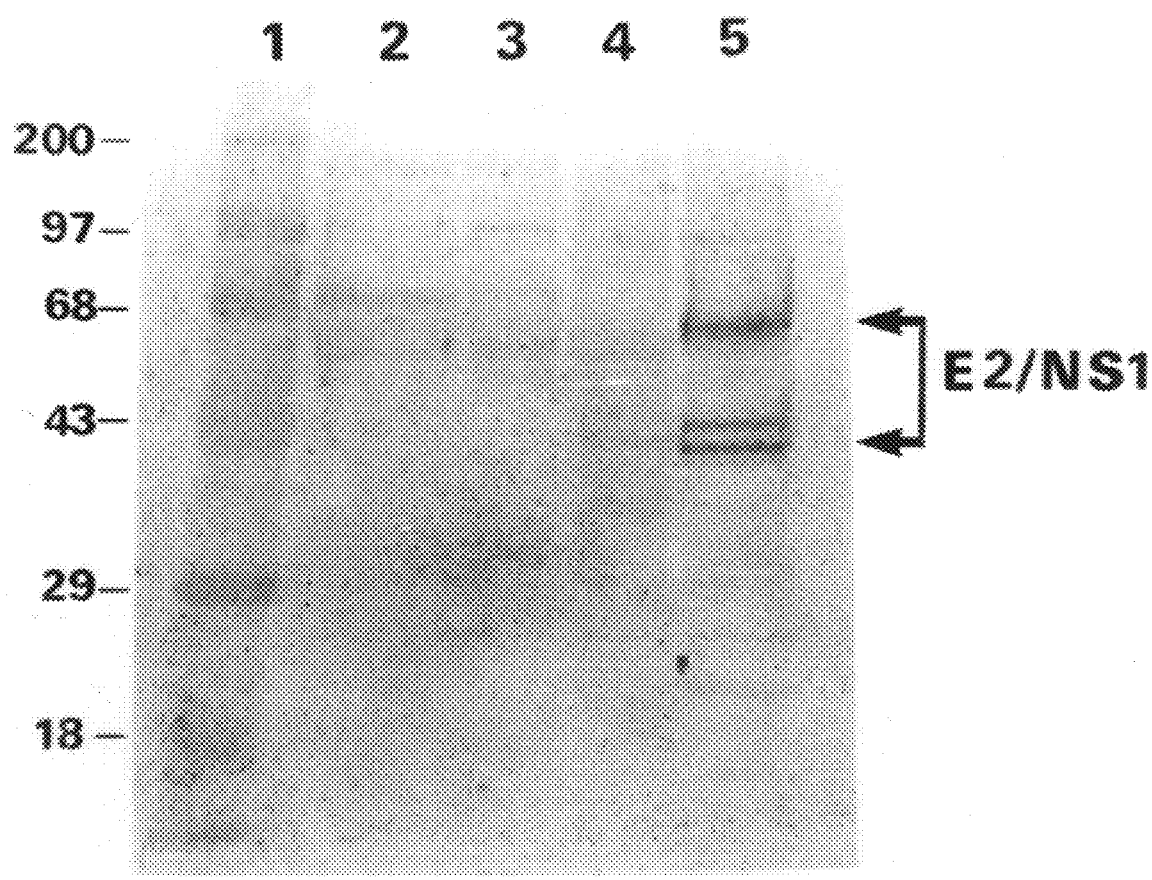

To clarify secretion of HCV E2/NS1 expressed from HCV E219, immunoblot analysis was carried out again by employing increased amount of extracellular protein (see: FIG. 4(B)). In FIG. 4(B), lanes are the same as lane 1, 2, 3, 4 and 5 in FIG. 4(A). As can be seen in FIG. 4(B), the molecular size of HCV E2/NS1 proteins ranges from 42 kDa to 72 kDa in the culture supernatant (42 kDa–72 kDa protein bands for HCV E2/NS1 are indicated by arrow heads).

Figure 5A:
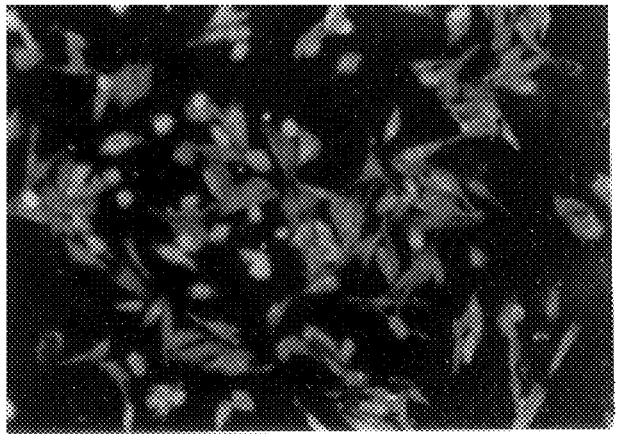
Figure 5B:
Figure 5C:

The expressed HCV E1 and E2/NS1 proteins were found as intracellular and extracellular proteins due to presumably a tPA-signal sequence, even though they were mostly inside the cell. To confirm residence of the expressed HCV E1 and E2/NS1 proteins inside the cell, immunofluorescence analysis of stable recombinant HCV E113 and HCV E219 cells were carried out (see: FIGS. 5(A), 5(B) and 5(C)). Each recombinant cell was fixed with acetone, or not fixed prior to indirected immunofluorescence analysis using the anti-HCV seropositive patient sera. FIGS. 5(A), 5(B) and 5(C) show immunofluorescence photographs of DHFR-positive CHO cells (control), HCV E113 and HCV E219, respectively. As can be seen in FIGS. 5(A), 5(B) and 5(C), it was determined that HCV E1 and E2/NS1 proteins are located around cell membrane.

EXAMPLE 5

Preparation of Unglycosylated HCV E1 and E2/NS1 Proteins

In order to verify that the incresed sizes of HCV E1 and E2/NS1 envelope glycoproteins expressed in Example 4 were attributed to N-linked glycosylation, the recombinant CHO cell lines were treated with tunicamycin, an antibiotic inhibitor of N-glycosylation which blocks the addition of N-acetylglucosamine to dolichol phosphate, the first step in the formation of the core oligosaccharide.

Figure 6A:
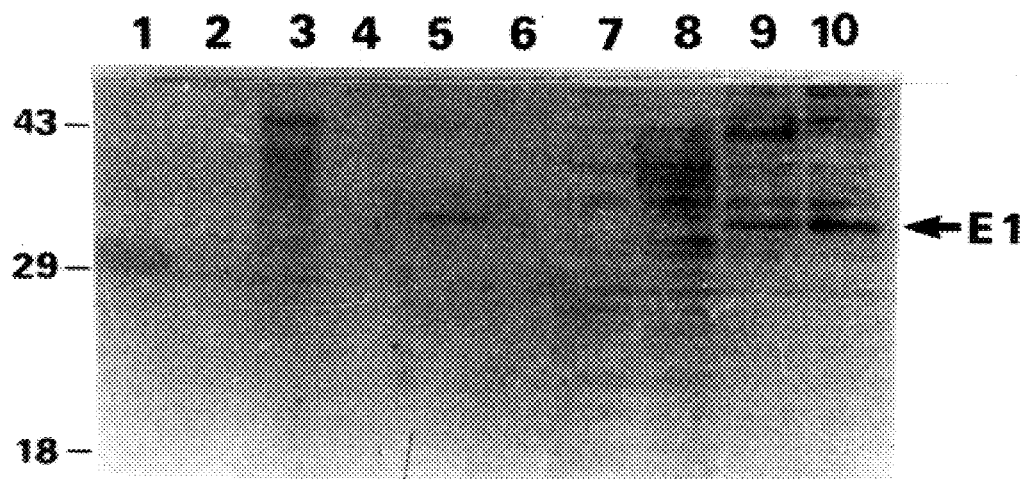
Figure 6B:
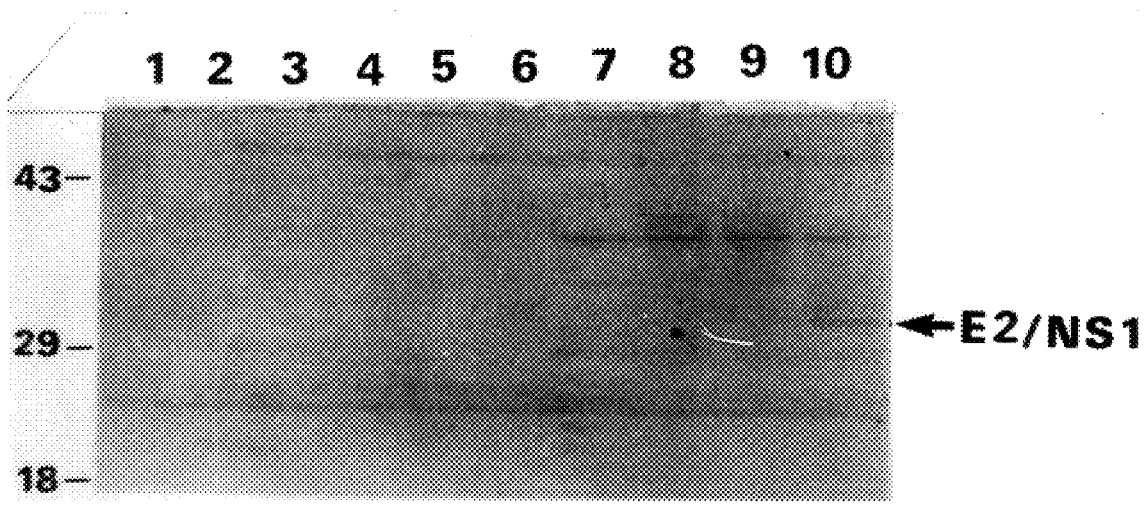

Transformed CHO cells were subcultured for 20 hrs before the treatment of tunicamycin at 5 ug per ml and maintained for another 6 hrs or 18 hrs. Cell lysate and the pellet of culture supernatant were suspended in lysis buffer containing 0.5% Triton X-100 for the electrophoresis on 10% SDS-PAGE. Glycosylation was almost completely inhibited after 18 hrs treatment of tunicamycin. Tunicamycin treatment gave unglycosylated proteins with decreased size of HCV E1 and E2/NS1 proteins to 33 kDa and 42 kDa, respectively (see: FIGS. 6(A) and 6(B)).

FIG. 6(A) shows immunoblot analysis results for HCV E1 protein expressed from HCV E1 stable cell line, i.e., HCV E113 adapted at 1 μM MTX. FIG. 6(B) shows immunoblot analysis results for HCV E2/NS1 expressed from HCV E2/NS1 stable cell line, i.e., HCV E219 adapted at 500 nM MTX. In FIG. 6(A), lane 1 is high molecular protein markers; lane 2 is the culture supernatant of nontransformed DHFR deficient CHO cells; lane 3 is the culture supernatant of HCV E113; lane 4 is the culture supernatant of HCV E113 treated with tunicamycin for 6 hrs; lane 5 is the culture supernatant of HCV E113 treated with tunicamycin for 18 hrs; lane 6 is empty; lane 7 is cell lysate of nontransformed DHFR deficient CHO cells; lane 8 is cell lysate of HCV E113; lane 9 is cell lysate of HCV E113 treated with tunicamycin for 6 hrs; and, lane 10 is cell lysate of HCV E113 treated with tunicamycin for 18 hrs. As can be seen in FIG. 6(A), the molecular size of unglycosylated E1 proteins is decreased to 33 kDa (unglycosylated E1 protein band is indicated by arrow head). In FIG. 6(B), lane 1 is high molecular protein markers; lane 2 is the culture supernatant of nontransformed DHFR deficient CHO cells; lane 3 is the culture supernatant of HCV E219; lane 4 is the culture supernatant of HCV E219 treated with tunicamycin for 6 hrs; lane 5 is the culture supernatant of HCV E219 treated with tunicamycin for 18 hrs; lane 6 is empty; lane 7 is cell lysate of nontransformed DHFR deficient CHO cells; lane 8 is cell lysate of HCV E219; lane 9 is cell lysate of HCV E219 treated with tunicamycin for 6 hrs; and, lane 10 is cell lysate of HCV E219 treated with tunicamycin for 18 hrs. As can be seen in FIG. 6(B), the molecular size of unglycosylated E2/NS1 proteins is decreased to 42 kDa (unglycosylated E2/NS1 protein band is indicated by arrow head).

As clearly illustrated and demonstrated as aboves, the present invention provides novel expression vectors for HCV E1 and E2/NS1 envelope glycoproteins, and a novel process for preparing HCV E1 and E2/NS1 proteins from CHO cells transformed with the said recombinant expression vectors. In accordance with the present invention, HCV E1 and E2/NS1 envelope glycoproteins can be produced in a massive manner from the transformed CHO cells; and, therefore, the recombinant HCV E1 and E2/NS1 envelope glycoproteins of the invention can be applied to the developement of a diagnostic reagent and a potential preventive HCV vaccine.

What is claimed is:

1. A process for preparing hepatitis C virus (HCV) envelope glycoprotein designated E1, which comprises the step of culturing Chinese Hamster Ovary (CHO) cells transformed with an expression vector which encodes HCV E1 envelope glycoprotein, wherein said E1 envelope glycoprotein is not expressed as part of a polyprotein, wherein said cells are cell line KCLRF-BP-00003 and said expression vector encoding said E1 glycoprotein is vector E113.

2. A process for preparing hepatitis C virus (HCV) envelope glycoprotein designated E2/NS1, which comprises the step of culturing Chinese Hamster Ovary (CHO) cells transformed with an expression vector which encodes full-length HCV E2/NS1 envelope glycoprotein, wherein said E2/NS1 envelope glycoprotein is not expressed as part of a polyprotein, wherein said cells are cell line KCLRF-BP-00004 and said expression vector encoding said E2/NS1 glycoprotein is vector E219.

3. The process of claim 1 wherein said expression vector comprises DNA encoding a 35 amino acid tPA signal sequence operably linked to DNA encoding said E1 glycoprotein; and said E1 glycoprotein is secreted from said cells.

4. The process of claim 2 wherein said expression vector comprises DNA encoding a 35 amino acid tPA signal sequence operably linked to DNA encoding said E2/NS1 glycoprotein; and said E2/NS1 glycoprotein is secreted from said cells.

5. The process of claim 3 which further comprises recovering said E1 glycoprotein expressed and secreted by said cells.

6. The process of claim 4 which further comprises recovering said E2/NS1 glycoprotein expressed and secreted by said cells.

* * * * *

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
(A) LENGTH: 576 base pairs
(B) TYPE: nucleic acid
(C) STRANDEDNESS: single
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(A) ORGANISM: Hepatitis C virus (vii) IMMEDIATE SOURCE:
(B) CLONE: seq.id.no.1

(xi) SEQUENCE DESCRIPTION: SEQ ID NO:1:

```
TACGAGGTGC GCAACGTGTC CGGGATATAC CATGTCACGA ACGACTGCTC CAACGCAAGC    60

ATTGTGTATG AGGCAGCGGA CTTGATTATG CATACCCCCG GGTGCGTGCC CTGCGTTCGG   120

GAGAGCAATA TTTCCCGTTG CTGGGTAGCG CTCACTCCCA CGCTCGCGGC CAGGAACGCC   180

ACCGTCCCCA CCACGACAAT ACGACGCCAC GTCGATTTGC TCGTTGGGGC GGCAGCTTTC   240

TGCTCCGCTA TGTACGTGGG AGACCTTTGC GGATCCGTTT TCCTCGTCTC CCAGTTGTTC   300

ACCTTTTCGC CTCGTCAGCA TGAGACGTTA CAGGACTGCA ACTGCTCAAT CTATCCCGGC   360
```

```
CACTTGTCAG GTCACCGCAT GGCATGGGAC ATGATGATGA ACTGGTCACC TACAACAGCC      420

CTACTACTGT CGCACTTACT CCGGATCCCA CAAGCTGTCT TGGACATGGT GGCAGGGGCC      480

CACTGGGGAG TCCTGGCGGG CCTCGCCTAC TATTCCATGG TGGGGAACTG GGCTAAGGTT      540

TTGATTGTGG TGCTGCTCTT TGCTGGCGTT GACGGG                                576
```

(2) INFORMATION FOR SEQ ID NO:2:

(i) SEQUENCE CHARACTERISTICS:
        (A) LENGTH: 1100 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Hepatitis C virus (vii) IMMEDIATE SOURCE:
        (B) CLONE: seq.id.no.2

(xi) SEQUENCE DESCRIPTION: SEQ ID NO:2:

```
CACACCCACG TGACAGGGGG AACGGCAGCC TATAACACCC GTGGGCTCAC AAGCCTCTTT       60

ACATTTGGGC CGTCTCAGAA AATCCAACTC ATAAATATTA ATGGCAGTTG GCACATCAAC      120

AGGACTGCCC TAAACTGCAA TGACTCCCTC CAAACTGGGT TTATTGCCGC GCTGTTCTAT      180

ACGCGCAGTT TCAACGCGTC CGGATGCCCA GAGCGCATGG CCAGTTGCCG CCCCATTGAC      240

AAGTTCGACC AGGGGTGGGG TTCCATCACC TATGCCGAGC CTGACAGCCT GGACCAGAGG      300

CCTTATTGCT GGCACTACCC ACCCCGACAG TGTGGTATCG TGCCAGCGTC GCAGGTGTGT      360

GGTCCGGTGT ATTGCTTCAC CCCGAGCCCT GTTGTCGTGG GGACGACCGA TCGGTTCGGT      420

GTCCCTACGT ATAGCTGGGG GGAGAACGTG ACTGATGTGC TGCTCCTTAA CAACACGCGG      480

CCGCCCCACA AGGACTGGTT CGGCTGTACA TGGATGAATA GCACTGGGTT CACCAAGACG      540

TGCGGGGGGC CCCGCTGTAA CATCGGGGGG CCGGCAACT ACACCTTGAC CTGCCCCACG      600

GACTGCTTCC GGAAGCACCC TGGGGCCACT TACACAAAAT GTGGTTCGGG GCCTTGGTTG      660

ACGCCTAGGT GCTTAGTTGA TTACCCATAC AGGCTATGGC ACTACCCCTG CACTGTCAAT      720

TTTTCCATCT TCAAGGTCAG GATGTACGTG GGGGGCGTGG AGCACAGGCT CAACGCTGCA      780

TGCAATTGGA CGCGAGGAGA GCGTTGTGCT TTGGAGGACA GGGATAGGTC GGAGCTCAGC      840

CCGCTGCTAC TGTCTACAAC AGAGTGGCAG ACGCTGCCCT GCTCCTTCAC CACCCTACCC      900

GCTTTGTCCA CTGGCTTGAT CCATCTCCAT CAGAACATTG TGGACATCCA ATACCTGTAC      960

GGTATAGGGT CAGCAGTTGT CTCCTTTGCA ATCAGATGGG AGTATGTCCT GTTGCTTTTC     1020

CTTCTCCTGG CGGACGCGCG CGTCTGCGCC TGCTTGTGGA TGATGCTGCT GATAGCCCAG     1080

GCTGAGGCCA CCTTAGAGAA                                                 1100
```

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA to mRNA

```
        (vi) ORIGINAL SOURCE:
              (A) ORGANISM: Hepatitis C virus (vii) IMMEDIATE SOURCE:
              (B) CLONE: SEQ.ID.NO.3

(xi) SEQUENCE DESCRIPTION: SEQ ID NO:3:

CAGGGAATCT GCCCGGTTGC                                               20

(2) INFORMATION FOR SEQ ID NO:4:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA to mRNA (vi) ORIGINAL SOURCE:
              (A) ORGANISM: Hepatitis C virus (vii) IMMEDIATE SOURCE:
              (B) CLONE: SEQ.ID.NO.4

(xi) SEQUENCE DESCRIPTION: SEQ ID NO:4:

GATGTGCCAG CTGCCGTTGG                                               20

(2) INFORMATION FOR SEQ ID NO:5:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA to mRNA (vi) ORIGINAL SOURCE:
              (A) ORGANISM: Hepatitis C virus (vii) IMMEDIATE SOURCE:
              (B) CLONE: SEQ.ID.NO.5

(xi) SEQUENCE DESCRIPTION: SEQ ID NO:5:

TACGAGGTGC GCAACGTGTC                                               20

(2) INFORMATION FOR SEQ ID NO:6:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA to mRNA (vi) ORIGINAL SOURCE:
              (A) ORGANISM: Hepatitis C virus (vii) IMMEDIATE SOURCE:
              (B) CLONE: SEQ.ID.NO.6

(xi) SEQUENCE DESCRIPTION: SEQ ID NO:6:

CCCGTCAACG CCAGCAAAGA                                               20

(2) INFORMATION FOR SEQ ID NO:7:

(i) SEQUENCE CHARACTERISTICS:
              (A) LENGTH: 20 base pairs
              (B) TYPE: nucleic acid
              (C) STRANDEDNESS: single
```

(D) TOPOLOGY: linear (ii) MOLECULE TYPE: cDNA to mRNA (vi) ORIGINAL SOURCE:
        (A) ORGANISM: Hepatitis C virus (vii) IMMEDIATE SOURCE:
        (B) CLONE: SEQ.ID.NO.7

(xi) SEQUENCE DESCRIPTION: SEQ ID NO:7:

TCTTTGCTGG CGTTGACGGG                                              20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA to mRNA (vi) ORIGINAL SOURCE:
        (A) ORGANISM: Hepatitis C virus (vii) IMMEDIATE SOURCE:
        (B) CLONE: SEQ.ID.NO.8

(xi) SEQUENCE DESCRIPTION: SEQ ID NO:8:

GCCGCATTGA GGACCACCAG                                              20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA to mRNA (vi) ORIGINAL SOURCE:
        (A) ORGANISM: Hepatitis C virus (vii) IMMEDIATE SOURCE:
        (B) CLONE: SEQ.ID.NO.9

(xi) SEQUENCE DESCRIPTION: SEQ ID NO:9:

CACACCCACG TGACAGGGGG                                              20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA to mRNA (vi) ORIGINAL SOURCE:
        (A) ORGANISM: Hepatitis C virus (vii) IMMEDIATE SOURCE:
        (B) CLONE: SEQ.ID.NO.10

(xi) SEQUENCE DESCRIPTION: SEQ ID NO:10:

GTTCTCTAAG GTGGCCTCAG                                              20

(2) INFORMATION FOR SEQ ID NO:11:

-continued

```
    (i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA to mRNA (vi) ORIGINAL SOURCE:
        (A) ORGANISM: Hepatitis C virus (vii) IMMEDIATE SOURCE:
        (B) CLONE: SEQ.ID.NO.11

(xi) SEQUENCE DESCRIPTION: SEQ ID NO:11:

GAGCTCGGAT CCATGTACGA GGTGCGCAAC GTGTC                                35

(2) INFORMATION FOR SEQ ID NO:12:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA to mRNA (vi) ORIGINAL SOURCE:
        (A) ORGANISM: Hepatitis C virus (vii) IMMEDIATE SOURCE:
        (B) CLONE: SEQ.ID.NO.12

(xi) SEQUENCE DESCRIPTION: SEQ ID NO:12:

GAGCTCGGAT CCTCACCCGT CAACGCCAGC AAAGA                                35

(2) INFORMATION FOR SEQ ID NO:13:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA to mRNA (vi) ORIGINAL SOURCE:
        (A) ORGANISM: Hepatitis C virus (vii) IMMEDIATE SOURCE:
        (B) CLONE: SEQ.ID.NO.13

(xi) SEQUENCE DESCRIPTION: SEQ ID NO:13:

GAGCTCGGAT CCATGCACAC CCACGTGACA GGGGG                                35

(2) INFORMATION FOR SEQ ID NO:14:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA to mRNA (vi) ORIGINAL SOURCE:
        (A) ORGANISM: Hepatitis C virus (vii) IMMEDIATE SOURCE:
        (B) CLONE: SEQ.ID.NO.14

(xi) SEQUENCE DESCRIPTION: SEQ ID NO:14:

GAGCTCGGAT CCTCAGTTCT CTAAGGTGGC CTCAG                                35
```

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA to mRNA (vi) ORIGINAL SOURCE:
        (A) ORGANISM: Hepatitis C virus (vii) IMMEDIATE SOURCE:
        (B) CLONE: SEQ.ID.NO.15

(xi) SEQUENCE DESCRIPTION: SEQ ID NO:15:

TACGAGGTGC GCAACGTGTC                                             20

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA to mRNA (vi) ORIGINAL SOURCE:
        (A) ORGANISM: Hepatitis C virus (vii) IMMEDIATE SOURCE:
        (B) CLONE: SEQ.ID.NO.16

(xi) SEQUENCE DESCRIPTION: SEQ ID NO:16:

CACACCCACG TGACAGGGGG                                             20

(2) INFORMATION FOR SEQ ID NO:17:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA to mRNA (vi) ORIGINAL SOURCE:
        (A) ORGANISM: Hepatitis C virus (vii) IMMEDIATE SOURCE:
        (B) CLONE: SEQ.ID.NO.17

(xi) SEQUENCE DESCRIPTION: SEQ ID NO:17:

GACTGAATTC ATGGATGCAA TGA                                         23

(2) INFORMATION FOR SEQ ID NO:18:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA to mRNA (vi) ORIGINAL SOURCE:
        (A) ORGANISM: Hepatitis C virus (vii) IMMEDIATE SOURCE:
        (B) CLONE: SEQ.ID.NO.18

-continued (xi) SEQUENCE DESCRIPTION: SEQ ID NO:18:

ACTGAAATCT CTGGCTCCTC TT 22